United States Patent [19]

Margalit

[11] Patent Number: 5,210,019

[45] Date of Patent: May 11, 1993

[54] PSEUDOMONAS SCREENING ASSAY

[75] Inventor: Ruth Margalit, San Marino, Calif.

[73] Assignee: The United States of America as represented by the Administrator of the National Aeronautics and Space Administration, Washington, D.C.

[21] Appl. No.: 501,908

[22] Filed: Mar. 30, 1990

[51] Int. Cl.$^5$ .......................................... G01N 33/569
[52] U.S. Cl. .................. 435/7.32; 435/7.92; 435/874; 436/518
[58] Field of Search .................... 435/7.32, 7.92, 7.94, 435/961; 436/530, 518

[56] References Cited

U.S. PATENT DOCUMENTS 4,963,480 10/1990 Belcour et al. ...................... 435/42

OTHER PUBLICATIONS

Stahey et al., J. Bacteriol., vol. 43, No. 2, pp. 149-154, (1942).
Trees et al., J. Inf. Dis., vol. 161, pp. 336-339. (1990).
A. B. Champion, K. L. Soderbere, & A. C. Wilson, "Immunological Comparison of Azurins of Known Amino Acid Sequence," J. Mol. Evol. 5, 291-305 (1975).
Nenad M. Kostic, Ruth Margalit, Chi-Ming Che & Harry B. Gray, "Kinetics of Long-Distance Ruthenium-to-Copper Electron Transfer in (Pentaammineruthenium histidine-83) Azurin", Journal of the American Chemical Society, 1983, 105, 7765.
D. Y. Mason, M. Naiem, Z. Abdulaziz, J. R. G. Nash, K. C. Gatter & H. Stein, Immuno histological Applications of Monoclonal Antibodies, pp. 585-613.
Joseph S. Lam, Lucy M. Mutharia & Robert E. W. Hancock, "Application of Monoclonal Antibodies to the Study of te Surface of Antigens in *Pseudomonas aeruginosa*, Monoclonal Antibodies Against Bacteria," vol. II, 143-157.

*Primary Examiner*—Esther L. Kepplinger
*Assistant Examiner*—Susan C. Wolski
*Attorney, Agent, or Firm*—Thomas H. Jones; John H. Kusmiss; Guy M. Miller

[57] ABSTRACT

A screening assay for detecting the presence of Pseudomonas bacteria in a test sample comprising isolating the bacteria present in the sample, extracting Azurin protein from the periplasm within the bacteria, reacting the extract with an enzymatically labelled, Azurin-specific antibody and a color-producing substrate specific for the enzyme which is capable of producing a color distinct from the color generated by Azurin and reading the results of the reaction of the sample with the antibody to determine whether the color has been produced whereby the presence of Pseudomonas bacteria in the sample is indicated.

15 Claims, No Drawings

PSEUDOMONAS SCREENING ASSAY

ORIGIN OF THE INVENTION

The invention described herein was made in the performance of work under a NASA contract, and is subject to the provisions of Public Law 96-517 (35 USC 202) in which the Contractor has elected not to retain title.

TECHNICAL FIELD

This invention relates to a method or test for the detection of Pseudomonas bacteria. More particularly, the invention relates to a Pseudomonas diagnostic assay involving the use of an Azurin-specific monoclonal antibody or antiserum for detection of the marker Azurin in Pseudomonas bacteria.

DISCUSSION OF THE PRIOR ART

The development of new diagnostic procedures for the rapid, accurate and cost efficient detection of the presence of bacteria which cause infection in susceptible hosts is a continuing concern for medical practitioners. For example, the early detection of the presence of Pseudomonas bacteria in a patient's system is particularly critical since strains of this bacteria are known to cause a large repertoire of virulent infections exhibiting high intrinsic resistance to antibiotic therapy and which demonstrate an adverse prognosis for cure if treatment is not initiated at as early a stage as possible. Exemplary of diseases associated with the Pseudo-monas bacteria are "Legionnaire's Disease", gram-negative septicemia and terminal lung disease in patients with cystic fibrosis. These infections spread extremely rapidly through-out a host's system once the bacteria is introduced therein. Accordingly, commencement of treatment at as early a stage as possible and, particularly, the early administration of a mixture of highly aggressive antibiotics is essential to thwart the spread of the disease.

Thus, it is especially important that the presence of the Pseudomonas bacteria in a host be reliably diagnosed at the earliest possible time so that appropriate treatment can be initiated immediately. Ideally, the diagnostic analysis of a specimen potentially carrying the bacteria should be capable of being completed on the same day it is taken from a patient to enable such a rapid treatment schedule. Present tests must be conducted by outside laboratories. It would be preferable to have a simple kit containing all the necessary reagents for conducting the test within the physician's office.

However, existing methods for detecting Pseudomonas bacteria have been found to be relatively tedious and time consuming which precludes immediate diagnosis. Furthermore, the prior techniques have been found to be rather inaccurate and unreliable as well as being expensive to perform. Specifically, the standard method for detection of Pseudomonas bacteria involves growing the bacteria on an agar plate, treating a polysaccharide capsule contained within the bacteria with reagent and reading the growth of the bacteria visually. This approach is relatively costly to perform and has been found to require a longer than desirable period of time to detect the presence of the bacteria which delays the commencement of the necessary antibiotic treatment. The previously standard test also has been found to be inaccurate and unreliable since it results in frequent false positive and false negative readings.

In addition to the aforementioned method, there also have been other previous attempts to create probes for the rapid and inexpensive detection of Pseudomonas bacteria. However, to date, none of these probes have proven sufficiently specific for clinical utilization.

STATEMENT OF THE INVENTION

The present invention provides a solution to the time, cost and reliability problems in the detection of Pseudomonas bacteria. Specifically, the present invention is directed to a diagnostic assay for Pseudomonas bacteria which is simple and inexpensive to perform. In contrast to prior procedures, the method of the present invention significantly reduces the time required to diagnose the bacteria and provides accurate and reliable test results.

The foregoing is achieved by a process which involves the use of Azurin, a blue, copper-containing monomeric protein specifically found in the Pseudomonas bacteria, as a specific marker for the immunological diagnosis of the presence of the Pseudomonas bacteria. More particularly, it has been found that Azurin can be readily extracted from the periplasm of Pseudomonas bacteria by a simple procedure. After extraction, the Azurin protein can be reliably, accurately and rapidly identified by treating a sample containing Azurin with an Azurin-specific monoclonal antibody or antiserum as tested in an enzyme-linked immunosorbent assay (ELISA).

Thus, in accordance with the present invention, the presence of Pseudomonas bacteria in a sample culture taken from the body fluids such as the mucus, urine, saliva, blood or an abscess of a patient can be conclusively established by treating the test sample to extract any Azurin present therein and applying the Azurin antiserum to identify whether any Azurin is actually present in the sample. From this diagnostic test, a positive indication of the presence of Azurin will establish the presence of the Pseudomonas bacteria whereas a negative showing will demonstrate that the bacteria is not present.

The preferred process for extracting and diagnosing the presence of Pseudomonas bacteria utilizing Azurin as a marker therefor generally comprises the steps of: (1) obtaining a test body fluid sample from a patient and spinning it down to isolate the bacteria therein; (2) shock treating the precipitate with water for the purpose of extraction of Azurin from the periplasm; (3) short spinning of the mixture to separate Azurin in the supernatant; (4) transferring a drop from (3) to a nitrocellulose membrane and incubating the membrane in a primary antibody solution (Anti-Azurin antibody); (5) preparing the membrane for enzymatic staining (wash) and (6) staining the membrane and reading the results to determine whether Pseudomonas bacteria were present in the test sample as evidenced by the presence of Azurin in the sample.

The primary antibody solution (Anti-Azurin antibody) for use in this process may be prepared in accordance with the method disclosed by A.B. Champion et al. in an article entitled "Immunological Comparison of Azurins of Known Amino Acid Sequence" which appeared in J. Mol. Evol. 5, 291–305 (1975). The method disclosed therein involved immunizing New Zealand white rabbits with purified Azurin for a period of 5 to 6 months. The Azurin may be initially obtained from aerobic bacteria such as Pseudomonas Auroginosa.

Generally, several white rabbits are immunized to compensate for the problem of anti-serum variability. Each rabbit receives between 0.2 and 1.0 mg of Azurin per injection. An initial intradermal back injection is made with Freund's complete adjuvant which is supplemented with 4 mg/ml lyophized phenol-killed BCG cells and the Azurin preparation is mixed in the (v/v) ration of 1.1/1, respectively.

After 10 to 12 weeks another intradermal injection is made with Freund's incomplete adjuvant. About 20 to 25 weeks subsequently to the last injection, a series of three intravenous injections are made a day apart in the rabbits' marginal ear vein. The rabbits are then bled one week after the last injection. Heparin solution that utilizes an isotris buffer is added in the amount of 1.0 ml per 1000 units/ml to each 40 ml of rabbit blood collected to prevent coagulation. It is common practice in some laboratories to use plasma instead of serum as the source of antibodies. Plasma and antiserum behave similarly in micro-complement fixation tests.

The heparin-rabbit blood solution is then centrifuged at $5000 \times g$ for 15 minutes to remove blood cells. The supernatant that results from this centrifugation is heated at 60° C. for 25 minutes to destroy the native rabbit complement. The treated solution is again centrifuged at $30,000 \times g$ for 20 minutes. The supernatant solution (antiserum) resulting from this centrifugation is stored at $-10°$ C.

An indication that the rabbit antiserum is pure is shown by a single precipitin arc that appears in double immuno-diffusion tests. Moreover, both pure Azurin and Azurins present in crude extracts give identical complement fixation curves.

EXAMPLE

In a preferred embodiment exemplifying the present invention, a body fluid sample of ~10 ml is taken from the urine or blood of a patient and any Pseudomonas strains in the sample are grown for 0-2 hours at room temperature until turbidity is noticed.

Subsequent to the incubation of the patient fluids, the resulting bacteria cells are harvested by centrifugation in an eppendorf (microfuge) spin at a rate of about $10,000-15,000 \times g$ for 0.5 minutes at room temperature. Following centrifugation, the pellet is resuspended by gentle mixing in 1 ml of distilled water. The cells are then centrifuged again for 3 minutes in the microfuge. After this centrifugation step, an aliquot (10 $\mu$l) of the supernatant is transferred by pipet to the nitrocellulose membrane for immunological detection.

The immunochemical detection of protein on the nitrocellulose membrane is accomplished by blocking the free binding sites on the membrane for 15 minutes with 3% bovine serum albumin and washed with water. The membrane is then incubated 1-2 hours at room temperature without shaking in primary monoclonal Anti-Azurin antibody solution which comprises 20 ml of 3% BSA/$H_2O$ and 50 $\mu$l of Anti-Azurin.

Subsequent to the incubation, the membrane is washed twice at room temperature with PBS or $H_2O$ for fifteen minute intervals. The membrane is then incubated at room temperature without shaking for 1-2 hours in secondary antibody solution which comprises 20 ml of 0.5% BSA/$H_2$ and 40 $\mu$l of serum. The serum comprises peroxidase anti-rabbit IgG antibody from Miles Scientific. The membrane is then washed at room temperature in a shaker with $H_2O$ for fifteen minutes.

The procedure of the preferred embodiment is completed with an enzymatic immunostaining of the membrane. In this regard, the enzyme used was horseradish peroxidase and the color developing reagent was 4-chloro-1-napthol (Sigma) in ethanol (3 mg/ml) formulated into a Tris-buffered saline solution as follows: 14.40 ml of water; 1.60 ml of tromethamine (Tris) having a pH of 7.6; 120 $\mu$l of 3% $H_2O_2$ and 4.0 ml 4-chloro-1-Napthol (Sigma) in ethanol which is stored at $-20°$ C. The nitrocellulose membrane is stained by gently shaking it in the solution for approximately two minutes. The staining reaction is terminated by placing the membrane in water for one minute.

After the staining process, the nitrocellulose membrane is examined to determine whether any Pseudomonas bacteria are present based on the detection of the presence of the Azurin marker. In this regard, the development of a blue color represents a positive result indicative of the presence of the Azurin protein which conclusively establishes the presence of Pseudomonas bacteria in the test sample.

From the foregoing, it will be appreciated that the present invention provides a significant improvement in test procedures for the detection of Pseudomonas bacteria. As will be noted, the present method enables expedited results with greatly enhanced accuracy in diagnosing the presence of this bacterial strain in a test sample taken from a patient. Particularly, it has been found that the use of a monoclonal antibody specific to the Azurin protein enabled the rapid screening of the Pseudomonas bacterial strains with accurate and reliable results which correlated well with those obtained utilizing immunofluorescence staining and chemical labeling techniques.

While there has been what is at present considered to be the preferred embodiment of this invention, it will be understood that various modifications may be made therein and it is intended to cover in the appended claims all such modifications as fall within the true spirit and scope of the invention.

I claim:

1. A screening assay for detecting the presence of Pseudomonas bacteria in a test sample comprising isolating the bacteria present in said sample, extracting Azurin protein from periplasm within the bacteria in said sample, reacting said extract with an enzymatically labelled, Azurin-specific antibody and a color-producing substrate specific for said enzyme and capable of producing a color distinct from the color generated by Azurin and reading the results of said reaction of said sample with said antibody to determine whether said color has been produced whereby the presence of Pseudomonas bacteria in said sample is indicated.

2. The diagnostic assay of claim 1 wherein said antibody is derived from rabbits or goats immunized with Azurin.

3. The diagnostic assay of claim 1 in which said antibody is a monoclonal antibody.

4. The screening assay of claim 1 wherein said test sample is a body fluid of a patient.

5. The diagnostic assay of claim 4 wherein the body fluid is selected from the group consisting of urine, blood, or pus of the patient.

6. The screening assay of claim 1 wherein said bacteria in said sample are directly isolated by centrifugation when said sample exhibits turbidity, or incubating said sample for up to 2 hours prior to said centrifugation until turbidity is evident.

7. The diagnostic assay of claim 6 wherein said antibody for reacting with said sample is derived from rabbits or goats immunized with Azurin.

8. The diagnostic assay of claim 6 wherein the presence of said Azurin extracted from said bacteria in said sample is detected by immobilizing said extracted Azurin on a membrane, blocking free binding sites on the membrane and reacting said membrane with said antibody.

9. The diagnostic assay of claim 8 wherein said membrane is nitrocellulose.

10. The diagnostic assay of claim 9 wherein horseradish peroxidase is employed as an enzyme for said enzymatic labelling and 4-chloro-1-napthol in a Tris-buffered saline solution is utilized as said color developing substrate.

11. A method for screening a body fluid for the presence of Pseudomonas bacteria utilizing Azurin as a marker for said bacteria comprising;
obtaining a test body fluid sample from a patient;
centrifuging said sample to isolate the bacteria therein and extracting the Azurin from said bacteria;
immobilizing the resulting Azurin extracted from said sample on a membrane;
contacting the membrane with an Azurin-specific, enzymatically labelled antibody solution; and
reacting the antibody with a color-producing substrate specific for said enzyme and capable of developing a color distinct from that of Azurin and reading the results to determine whether Pseudomonas bacteria were present in the test sample as evidenced by the presence of said color on the membrane.

12. The method of claim 11 in which the membrane is nitrocellolose.

13. The method of claim 11 wherein said test body fluid sample is selected from the group consisting of urine, blood or pus of the patient.

14. The method of claim 11 wherein horseradish peroxidase is employed as an enzyme for labelling said antibody and 4-chloro-1-napthol in a Tris-buffered saline solution is utilized as said color developing substrate.

15. A method according to claim 11 in which the antibody is a monoclonal antibody.

* * * * *